(12) United States Patent
Lukesh, III (10) Patent No.: US 11,931,428 B2
(45) Date of Patent: Mar. 19, 2024

(54) SELECTIVE HYDROGEN SULFIDE PROBE AND USES THEREOF

(71) Applicant: Wake Forest University Health Sciences, Winston-Salem, NC (US)

(72) Inventor: John C. Lukesh, III, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 706 days.

(21) Appl. No.: 16/947,869

(22) Filed: Aug. 21, 2020

(65) Prior Publication Data
US 2021/0052746 A1 Feb. 25, 2021

Related U.S. Application Data

(60) Provisional application No. 62/891,047, filed on Aug. 23, 2019.

(51) Int. Cl.
| | |
|---|---|
| *C07F 11/00* | (2006.01) |
| *A61K 9/00* | (2006.01) |
| *A61K 49/00* | (2006.01) |
| *A61K 49/10* | (2006.01) |

(52) U.S. Cl.
CPC ........ *A61K 49/0039* (2013.01); *A61K 9/0019* (2013.01); *A61K 9/0053* (2013.01); *C07F 11/00* (2013.01)

(58) Field of Classification Search
CPC ............. G01N 33/6893; G01N 33/574; G01N 33/5091; G01N 33/6896; G01N 33/497; G01N 2033/4977; G01N 33/0044; A61K 9/0053; A61K 9/0019; A61K 49/0039;
(Continued)

(56) References Cited

U.S. PATENT DOCUMENTS

| | | |
|---|---|---|
| 5,696,126 A | 12/1997 | Chenard |
| 6,680,299 B2 | 1/2004 | Or et al. |
| 2016/0129111 A1 | 5/2016 | Ghandehari et al. |

(Continued)

FOREIGN PATENT DOCUMENTS

| | | | | |
|---|---|---|---|---|
| CN | 107441042 A | * | 12/2017 | ........... A61K 31/704 |
| WO | WO-2005000862 A2 | * | 1/2005 | ............... C07H 5/10 |

OTHER PUBLICATIONS

Haratake et al. Synthesis of Nanovesicular Glutathione Peroxidase Mimics with a Selenenylsulfide-Bearing Lipid. ACS Omega 2016, vol. 1, pp. 58-65. (Year: 2016).*

(Continued)

*Primary Examiner* — Shafiqul Haq
(74) *Attorney, Agent, or Firm* — Myers Bigel, P.A.

(57) ABSTRACT

Provided herein is a compound of formula I:

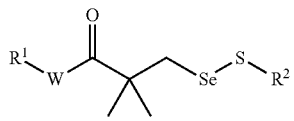

and the use thereof for detecting the presence of hydrogen sulfide in cells or tissues in vitro or in vivo. The detecting may be useful, for example, in diagnosing cancer or other diseases related to imbalanced hydrogen sulfide ($H_2S$) production such as neurodegenerative diseases.

13 Claims, 4 Drawing Sheets

(58) Field of Classification Search
CPC .. A61K 49/0028; A61K 49/0052; C07F 11/00
See application file for complete search history.

(56) References Cited

U.S. PATENT DOCUMENTS

| | | |
|---|---|---|
| 2017/0216451 A1 | 8/2017 | Naleway et al. |
| 2018/0207287 A1 | 7/2018 | Naleway et al. |
| 2018/0306792 A1 | 10/2018 | Bhuniya et al. |
| 2020/0010432 A1 | 1/2020 | Huigens et al. |

OTHER PUBLICATIONS

Telele et al. Natural-Products-Inspired Use of the gem-Dimethyl Group in Medicinal Chemistry. J. Med. Chem. 2018, 61, pp. 2166-2210. (Year: 2018).*

Wang et al. Dual-Function Fluorescent Probe for Detection of Hydrogen Sulfide and Water Content in Dimethyl Sulfoxide. ACS Omega 2019, vol. 4, pp. 10695-10701. (Year: 2019).*

Cai et al. "Hydrogen sulfide induces human colon cancer cell proliferation: Role of Akt, ERK and p21" Cell Biol. Int., 34(6): 565-572 (2010).

Cao et al. "A Review of Hydrogen Sulfide Synthesis, Metabolism, and Measurement: Is Modulation of Hydrogen Sulfide a Novel Therapeutic for Cancer?" Antiox. Redox Signal, 31(1): 1-38 (2019).

Cao et al. "Butyrate-stimulated [H.sub.2]S production in colon cancer cells" Antiox. Redox Signal., 12(9): 1101-1109 (2010).

Chan et al. "Reaction-based small-molecule fluorescent probes for chemoselective bioimaging" Nat. Chem., 4(12):973-984 (2012).

Chao et al. "Cystathionine-β-Synthase Inhibition for Colon Cancer: Enhancement of the Efficacy of Aminooxyacetic Acid via the Prodrug Approach" Mol. Med., 22, 361-379 (2016).

Ferriz et al., "Prodrug Design of Phenolic Drugs" Current Pharmaceutical Design, 16(18): 2033-2052(20) (2010). Abstract.

Filipovic et al. "Chemical Biology of H2S Signaling through Persulfidation" Chem. Rev., 118: 1253-1337 (2018).

Hansen et al. "Folic acid mediates activation of the pro-oncogene STAT3 via the Folate Receptor alpha" Cell. Signal., 27(7): 1356-1368 (2015).

Huang et al. "Aldehyde group assisted thiolysis of dinitrophenyl ether: a new promising approach for efficient hydrogen sulfide probes" Chem. Commun., 50: 9185-9187 (2014).

Hughes et al. "Making and working with hydrogen sulfide: The chemistry and generation of hydrogen sulfide in vitro and its measurement in vivo: A review" Free Radic. Biology. Med.., 47(10): 1346-1353 (2009).

Jung et al. "Gem-Disubstituent Effect: Theoretical Basis and Synthetic Applications" Chem. Rev., 105(5): 1735-1766 (2005).

Kimura, H. "Hydrogen sulfide: its production, release and functions" Amino Acids, 41: 113-121 (2011).

Lee et al. "Fluorogenic Reaction-Based Prodrug Conjugates as Targeted Cancer Theranostics" Chem. Soc. Rev., 47(1): 28-52 (2018).

Lin et al. "Chapter Four—Azide-Based Fluorescent Probes: Imaging Hydrogen Sulfide in Living Systems" Methods in Enzymology, Elsevier, 554: 63-80 (2015).

Lin et al. "Chemical probes for molecular imaging and detection of hydrogen sulfide and reactive sulfur species in biological systems" Chem. Soc. Rev., 44: 4596-4618 (2015).

Lin et al. "Fluorescent probes for sensing and imaging biological hydrogen sulfide" Curr. Opin. Chem. Biol., 16(5-6):595-601 (2012).

Lippert, A.R. "Designing reaction-based fluorescent probes for selective hydrogen sulfide detection" J. Inorg. Biochem., 133: 136-142 (2014).

Lippert et al. "Reaction-Based Fluorescent Probes for Selective Imaging of Hydrogen Sulfide in Living Cells" J. Am. Chem. Soc., 133(26): 10078-10080 (2011).

Liu et al. "Capture and Visualization of Hydrogen Sulfide via A Fluorescent Probe" Angew. Chem. Int. Ed., 50(44):10327-10329 (2011).

Liu et al. "Reaction Based Fluorescent Probes for Hydrogen Sulfide" Org. Lett., 14(8): 2184-2187 (2012).

Lukesh et al. "Thiols and Selenols as Electron-Relay Catalysts for Disulfide-Bond Reduction" Angew. Chem. Int. Ed., 125(49): 13139-13142 (2013).

Módis et al. "Effect of S-adenosyl-L-methionine (SAM), an allosteric activator of cystathionine-β-synthase (CBS) on colorectal cancer cell proliferation and bioenergetics in vitro" Nitric Oxide, 41: 146-156 (2014).

Peng et al. "Chapter Three—Hydrogen Sulfide Detection Using Nucleophilic Substitution-Cyclization-Based Fluorescent Probes" Methods in Enzymology, Elsevier, 554: 47-62 (2015). Abstract.

Peng et al. "Fluorescent Probes Based on Nucleophilic Substitution-Cyclization for Hydrogen Sulfide Detection and Bioimaging" Chem., 20(4): 1010-1016 (2014).

Peng et al. "Trapping Hydrogen Sulfide (H2S) with Diselenides: The Application in the Design of Fluorescent Probes" Org. Lett., 17(6): 1541-1544 (2015).

Qian et al. "Selective fluorescent probes for live-cell monitoring of sulphide" Nat. Commun., 2, 495 (2011) (7 pages).

Reich et al. "Why Nature Chose Selenium" ACS Chem. Biol., 11: 821-841 (2016).

Ren et al. "Recent development of biotin conjugation in biological imaging, sensing, and target delivery" Chem. Commun., 51: 10403-10418 (2015).

Shams et al. "Treatment of corneal cystine crystal accumulation in patients with cystinosis" Clin Ophthalmol., 8: 2077-2084 (2014).

Song et al. "A cancer cell-specific two-photon fluorescent probe for imaging hydrogen sulfide in living cells" RSC Adv., 7: 15817-15822 (2017).

Steinmann et al. "Selenium and Sulfur in Exchange Reactions: A Comparative Study" J. Org. Chem., 75(19): 6696-6699 (2010).

Suarez et al. "Selenosulfides Tethered to gem-Dimethyl Esters: A Robust and Highly Versaitile Framework for H2S Probe Development" Chem. Eur. J., 25(69):15736-15740 (2019). Abstract.

Szabo et al. "Tumor-derived hydrogen sulfide, produced by cystathionine-β-synthase, stimulates bioenergetics, cell proliferation, and angiogenesis in colon cancer" Proc. Natl. Acad. Sci. USA, 110(30): 12474-12479 (2013).

Talele, T.T. "Natural-Products-Inspired Use of the gem-Dimethyl Group in Medicinal Chemistry" J. Med. Chem., 61(6): 2166-2210 (2018).

Wu et al. "Hydrogen sulfide in cancer: Friend or foe?" Nitric Oxide, 50(15): 38-45 (2015).

Xuan et al. "Fluorescent Probes for the Detection of Hydrogen Sulfide in Biological Systems" Angew. Chem. Int. Ed., 51(10): 2282-2284(2012).

Yang et al. "Data-Driven Identification of Hydrogen Sulfide Scavengers" Angew. Chem. Int. Ed., 58(32): 10898-10902 (2019).

Zhang et al. "Dual-biomarker-triggered fluorescence probes for differentiating cancer cells and revealing synergistic antioxidant effects under oxidative stress" Chem. Sci., 10(7): 1945-1952 (2019).

* cited by examiner

SELECTIVE HYDROGEN SULFIDE PROBE AND USES THEREOF

CROSS-REFERENCE TO RELATED APPLICATIONS

This application claims the benefit of U.S. Provisional Patent Application No. 62/891,047, filed Aug. 23, 2019, the disclosure of which is incorporated by reference herein in its entirety.

BACKGROUND

Hydrogen sulfide ($H_2S$), once regarded as merely a toxic and foul-smelling gas, has recently been recognized as an endogenous signaling molecule and important physiological mediator within mammalian systems. H. Kimura, Amino Acids 2011, 41, 113-121; M. R. Filipovic et al, Chem. Rev. 2018, 118, 1253-1337; X. Cao et al, Antiox. Redox Signal. 2019, 31, 1-38. Although several $H_2S$-regulated processes have been discovered in recent years, questions surrounding its metabolism, distribution, and prevalence still persist. Therefore, the development of new bioanalytical methods for probing the biological signaling pathways of $H_2S$ is needed to better discern its primary and secondary roles as a signaling molecule. To this end, reaction-based fluorescent probes have proven to be invaluable chemical tools for aiding $H_2S$ research by providing a non-destructive method for the real-time detection and visualization of $H_2S$ within biological samples. J. Chan et al, Nat. Chem. 2012, 4, 973-984; V. S. Lin, C. J. Chang, Curr. Opin. Chem. Biol. 2012, 16, 595-601; B. Peng, M. Xian, in Methods in Enzymology, Elsevier, 2015, pp. 47-62; W. Xuan et al, Angew. Chem. Int. Ed. 2012, 51, 2282-2284; V. S. Lin et al, Chem. Soc. Rev. 2015, 44, 4596-4618; V. S. Lin et al, in Methods in Enzymology, Elsevier, 2015, pp. 63-80; A. R. Lippert, J. Inorg. Biochem. 2014, 133, 136-142.

Developing reaction-based probes that can selectively detect $H_2S$ within a biological setting, however, does pose significant challenges. With other biological thiols being present in appreciably higher concentrations (e.g. glutathione), reaction-based probes must effectively key in on reactivity differences that distinguish $H_2S$ from these other species. With a suppressed pKa (6.8) relative to that of other biothiols (pKa: ~8-9), $H_2S$ resides predominately in its reactive HS-form under physiological conditions, rendering it a vastly superior reductant and nucleophile at neutral pH. M. N. Hughes et al, Free Radic. Biol. Med. 2009, 47, 1346-1353. Chang and co-workers were the first to develop a turn-on fluorescent probe that capitalized on this increased reactivity with their design of an azide-caged rhodamine dye. A. R. Lippert, E. J. New, C. J. Chang, J. Am. Chem. Soc. 2011, 133, 10078-10080. With the addition of $H_2S$, reduction of the aryl azide to the aryl amine afforded a significant increase in fluorescence intensity upon a 30-60 min incubation period. In an alternative approach, Xian and He were the first to develop reaction-based probes that relied on cascade processes to release a fluorescent reporter. Y. Qian et al, Nat. Commun. 2011, 2, 495; C. Liu et al, Angew. Chem. Int. Ed. 2011, 50, 10327-10329; C. Liu et al, Org. Lett. 2012, 14, 2184-2187; B. Peng et al, Chem.—Eur. J. 2014, 20, 1010-1016; Z. Huang et al, Chem. Commun. 2014, 50, 9185-9187; B. Peng et al, Org. Lett. 2015, 17, 1541-1544. These probes also displayed good selectivity as they effectively exploited the double nucleophilic character of $H_2S$ another distinctive feature of its reactivity.

Still, with low water solubility and inefficient intracellular delivery, many $H_2S$-reactive probes have proven unsuccessful in their ability to function in a biological setting. The extreme hydrophobic nature of some even required the use of an organic co-solvent (such as acetonitrile) for in vitro assays or surfactants for cellular assays. B. Peng, M. Xian, in Methods in Enzymology, Elsevier, 2015, pp. 47-62. Moreover, the ability of $H_2S$-responsive probes to target specific tissues or cell types, especially where $H_2S$ is highly expressed, has been virtually unexplored thus far. This precise delivery, however, would likely facilitate the tracking of $H_2S$ dynamics in vivo, providing a clearer understanding of its production, metabolism, and mechanism of action.

Therefore, the continued development of reaction-based fluorescent probes with improved physicochemical properties is highly desirable and would provide a significant contribution to the chemical toolkit that is currently available for studying $H_2S$ physiology.

SUMMARY

Provided herein according to embodiments is a compound of formula I:

wherein:
- $R^1$ is H, alkyl, aryl, heteroaryl, halogen, a prodrug, or a reporter moiety;
- $R^2$ is a physicochemical modulator; and
- W is O, S, or NH, or a pharmaceutically acceptable salt thereof.

In some embodiments, $R^1$ is a fluorescent reporter moiety. In some embodiments, the fluorescent reporter moiety is fluorescent upon cleavage from the compound of formula I upon reaction with hydrogen sulfide ($H_2S$).

In some embodiments, the fluorescent reporter moiety is:

In some embodiments, the fluorescent reporter moiety is:

In some embodiments, the fluorescent reporter moiety is:

In some embodiments, the fluorescent reporter moiety is:

In some embodiments, the physicochemical modulator is:

In some embodiments, the physicochemical modulator is:

In some embodiments, the physicochemical modulator is a targeting group. In some embodiments, the targeting group is:

In some embodiments, the targeting group is:

Also provided is a method of detecting the presence of hydrogen sulfide ($H_2S$) in cells or tissues in vitro or in vivo, comprising contacting the cells or tissues with a compound as taught herein. In some embodiments, the detecting comprises detecting in particular cell type(s) and/or specific organelle(s).

DETAILED DESCRIPTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The disclosures of all patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise.

Subjects, tissues, cells and proteins utilized to carry out the present invention may be of any suitable source including microbial (including gram negative and gram positive bacteria, yeast, algae, fungi, protozoa, and viral, etc.), plant (including both monocots and dicots) and animal (including mammalian, avian, reptile, and amphibian species, etc.) Mammalian subjects include both humans and other animal species treated for veterinary purposes (including but not limited to monkeys, dogs, cats, cattle, horses, sheep, rats, mice, rabbits, goats, etc.). In some embodiments, human subjects are preferred.

As used herein in the accompanying chemical structures, "H" refers to a hydrogen atom. "C" refers to a carbon atom. "N" refers to a nitrogen atom. "S" refers to a sulfur atom. "0" refers to an oxygen atom.

"Alkyl," as used herein, refers to a saturated straight or branched chain, or cyclic hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, cyclopropyl, cyclobutyl, cyclopentyl, cyclohexyl, and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, cyclopropyl, cyclobutyl, and the like. The alkyl groups may be optionally substituted with one or more suitable substituents, such as halo, hydroxy, carboxy, amine, etc.

"Aryl," as used herein, refers to a monocyclic carbocyclic ring system or a bicyclic carbocyclic fused or directly adjoining ring system having one or more aromatic rings. Examples include, but are not limited to, phenyl, indanyl, indenyl, tetrahydronaphthyl, and the like. As noted, in some embodiments, the aryl has two aromatic rings, which rings are fused or directly adjoining. Examples include, but are not limited to, biphenyl, napthyl, azulenyl, etc. The aryl may be optionally substituted with one or more suitable substituents, such as alkyl, halo, hydroxy, carboxy, amine, etc.

"Heteroaryl," as used herein, refers to a monovalent aromatic group having a single ring or two fused or directly adjoining rings and containing in at least one of the rings at least one heteroatom (typically 1 to 3) independently selected from nitrogen, oxygen and sulfur. Examples include, but are not limited to, pyrrole, imidazole, thiazole, oxazole, furan, thiophene, triazole, pyrazole, isoxazole, isothiazole, pyridine, pyrazine, pyridazine, pyrimidine, triazine, and the like. As noted, in some embodiments, the heteroaryl has two aromatic rings, which rings are fused or directly adjoining. Examples include, but are not limited to, benzothiophene, benzofuran, indole, benzimidazole, benzothiazole, quinoline, isoquinoline, quinazoline, quinoxaline, phenyl-pyrrole, phenyl-thiophene, etc. The heteroaryl may be optionally substituted with one or more suitable substituents, such as alkyl, halo, hydroxy, carboxy, amine, etc.

The terms "halo" and "halogen," as used herein, refer to fluoro (—F), choro (—Cl), bromo (—Br), or iodo (—I).

As understood in the art, the term "optionally substituted" indicates that the specified group is either unsubstituted, or substituted by one or more suitable substituents. A "sub-stituent" that is "substituted" is a group which takes the place of one or more hydrogen atoms on the parent organic molecule.

"Selenosulfide," as used herein, is a moiety of the general structure R'—S—Se—R", wherein R' and R" are independently selected from H or optionally substituted alkyl, aryl, or heteroaryl. In some embodiments, the selenium of formula I is made more electrophilic by an organic substituent. In some embodiments, the selenium byproduct from the reaction of a compound of formula I with hydrogen sulfide ($H_2S$) is less reactive with hydrogen sulfide ($H_2S$) than its parent compound of formula I. In some embodiments, the selenium byproduct from the reaction of a compound of formula I with hydrogen sulfide ($H_2S$) will not react any further with additional hydrogen sulfide ($H_2S$).

I. Active Compounds.

Provided herein according to embodiments is a compound of formula I:

wherein:
$R^1$ is H, alkyl, aryl, heteroaryl, halogen, a prodrug, or a reporter moiety;
$R^2$ is a physicochemical modulator; and
W is O, S, or NH,
or a pharmaceutically acceptable salt thereof.

The compounds as taught herein may be provided in a salt form such as a pharmaceutically acceptable salt. A "pharmaceutically acceptable salt" is a salt that retains the biological effectiveness of the free acids and bases of a specified compound and that is not biologically or otherwise undesirable. Examples of pharmaceutically acceptable salts include but are not limited to sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

As used herein, the phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

"Prodrug" as used herein is a drug or pharmaceutical agent that is inactive in its administered form, but becomes a pharmacologically active agent by a metabolic or physicochemical transformation. A thorough discussion is provided in T. Higuchi and V. Stella, Prodrugs as Novel delivery Systems, Vol. 14 of the A.C.S. Symposium Series and in

Edward B. Roche, ed., Bioreversible Carriers in Drug Design, American Pharmaceutical Association and Pergamon Press, 1987, both of which are incorporated by reference herein in their entireties. See also US 2020/0010432 to Huigens, III, et al., U.S. Pat. Nos. 5,696,126 and 6,680,299, and "Prodrug Design of Phenolic Drugs," DOI: 10.2174/138161210791293042, herein incorporated by reference.

"Reporter moiety" as used herein in a moiety that is detectable upon reaction of the compound with hydrogen sulfide ($H_2S$).

In some embodiments, $R^1$ is a fluorescent reporter moiety. In some embodiments, fluorescent reporter moiety is fluorescent upon cleavage from the compound of formula I upon reaction with hydrogen sulfide ($H_2S$). In some embodiments, the fluorescent reporter moiety is:

In some embodiments, the fluorescent reporter moiety is:

In some embodiments, the fluorescent reporter moiety is:

In some embodiments, the fluorescent reporter moiety is:

"Physicochemical modulator" may be any suitable hydrocarbyl group (e.g., an aliphatic hydrocarbon group with one or more heteroatoms selected from O and N, which may aid in solubility of the compound) and/or covalently attached targeting group. In some embodiments, $R^2$ comprises a targeting group. In some embodiments, targeting group is targeted to specific cell type(s) and/or specific organelle(s) (e.g., biotin or other cancer cell specific ligand, or a targeting peptide or nucleic acid (such as an aptamer)). See, e.g., U.S. 2018/0207287 to Naleway et al.; US 2017/0216451 to Naleway et al.; 2016/0129111 to Ghanderhari et al.; which are incorporated by reference herein.

In some embodiments, the physicochemical modulator is a pharmaceutical agent, a diagnostic marker, a chemotherapeutic drug, a monoclonal antibody, a cofactor, a conjugate, a vitamin, D-biotin, folic acid, or a combination thereof.

In some embodiments, the physicochemical modulator is:

In some embodiments, the physicochemical modulator is:

In some embodiments, the physicochemical modulator is mitochondria-targeting. In some embodiments, the mitochondria-targeting physicochemical modulator is:

In some embodiments, the physicochemical modulator is lysosomal-targeting. In some embodiments, the lysosomal-targeting physicochemical modulator is:

Particular examples of formula I include, but are not limited to:

and pharmaceutically acceptable salts or prodrugs thereof.

Methods of synthesizing the compounds as taught herein may be found in Suarez et al., "Selenosulfides Tethered to gem-Dimethyl Esters: A Robust and Highly Versatile Framework for $H_2S$ Probe Development," *Chem. Eur. J.,* 25:15736-15740 (2019), and are incorporated herein by reference. A skilled artisan would recognize that multiple synthetic pathways are possible to prepare a compound of formula (I) and thus, the current invention is not limited to any particular method of synthesizing a compound of formula (I).

In some embodiments, the active compound as taught herein is stable over a pH range of 4 to 9. In some embodiments, the active compound as taught herein is stable over a pH range of 6 to 8. In other embodiments, the compound is stable in physiological conditions. In some embodiments, the compound is stable in acidic conditions such as in tumor microenvironment.

II. Methods of Use for Detecting $H_2S$.

Provided are methods of detecting the presence of hydrogen sulfide ($H_2S$) in cells or tissues in vitro or in vivo, comprising contacting the cells or tissues with a compound as taught herein. In some embodiments, the detecting comprises detecting in particular cell type(s) and/or specific organelle(s).

The cells may include cancer cells, cells from adipose, muscle, cartilage, bone, mucosa, lung, heart cells, brain, liver, kidney, pancreas, vasculature tissues, or a combination thereof. The active compound as taught herein may be at least 100 to 1000 fold selective for hydrogen sulfide over cysteine (Cys), $H_2O_2$, $NaNO_2$, $Cu(OAc)_2$, $Zn(OAc)_2$, $FeSO_4$, $FeCl_3$, $Na_2CO_3$, GSH, or ascorbic acid (AA). The suitable amount of the compound may be in the range of 10-600 μM.

Hydrogen sulfide ($H_2S$) plays a key role in cellular signaling events such as a neurotransmitter in central nervous system of humans and mammals. See US 2018/0306792 to Bhuniya et al. $H_2S$ is generated in vivo enzymatically from sulfur containing amino acids such as cysteine and homocysteine in the presence of enzymes such as cystathionine-beta-synthase (CBS), cystathionine-gamma-lyase (CSE), and 3-mercaptopyruvate sulfurtransferase in a controlled manner in several organs such as heart, vasculature, brain, kidney, liver, lungs, pancreas, thoracic aorta, ileum, portal vein, and uterus. It can also be produced via non-enzymatic pathways and from the bacterial conversion of dietary substrates. Recent studies have revealed that an imbalance in production of $H_2S$ is linked to several diseases, including Alzheimer's disease, Parkinson's disease and other neurodegenerative diseases, along with possible risk for diabetes, arterial and pulmonary hypertension, dementia, diseases such as cirrhosis and gastric mucosal injury, etc.

Hydrogen sulfide may be detected in a sample, which may include the steps of: providing the sample comprising a population of cells; contacting the sample with a composition comprising a suitable amount of a compound of formula I, or a pharmaceutically acceptable salt thereof (e.g. for a predetermined time period); and detecting a change in fluorescence for the sample using a fluorescence detector. In some embodiments, the sample is excited in the range of 300-550 nm and the emission is detected in the range of 300-550 nm. The method may include visualizing the change in fluorescence using microscopy. The population of cells may include cancer cells, cells from adipose, muscle, cartilage, bone, mucosa, lung, heart cells, brain, liver, kidney, pancreas, or vasculature, or a combination thereof. The method may include determining the change in fluorescence of the sample is greater than that of a standard sample, with the change in fluorescence indicative of disease, relapse or outcome.

The active compounds taught herein are useful in methods of imaging cells, particularly cells having increased expression of hydrogen sulfide ($H_2S$)-producing enzymes. Such methods of imaging may include steps of contacting cells with an effective amount of a compound of the invention and then measuring fluorescence emitted by the compound using any known methods in the art.

The levels of hydrogen sulfide ($H_2S$) in a cell can very. For example, a healthy cell typically has a lower hydrogen sulfide ($H_2S$) level compared to a diseased cell (e.g., a cancerous cell). In another example, the hydrogen sulfide ($H_2S$) level of two different types of diseased cells (e.g., two different cancerous cells) can vary, as well. The methods of the invention are able to differentiate between a healthy cell and a diseased cell or two different types of diseased cells based on the cellular uptake of the compounds of the invention due to the different levels of hydrogen sulfide ($H_2S$) present in each cell.

In some embodiments, cellular uptake of the compound of the invention into a diseased cell (e.g., a cancerous cell) is higher compared to the cellular uptake of the compound of the invention into a healthy cell. In some embodiments, the cellular uptake of the compound of the invention into a diseased cell is about 2-fold, about 3-fold, about 4-fold, about 5-fold, about 6-fold, about 7-fold, about 8-fold, about 9-fold, or about 10-fold higher compared to the cellular of the compound of the invention into a healthy cell.

In some embodiments, cellular uptake of the compound of the invention into a first diseased cell (e.g., a cancerous cell) is higher compared to the cellular uptake of the compound of the invention into a second diseased cell, wherein the first diseased cell is different compared to the second diseased cell. In some embodiments, the cellular uptake of the compound of the invention into a first diseased cell is about 2-fold, about 3-fold, about 4-fold, about 5-fold, about 6-fold, about 7-fold, about 8-fold, about 9-fold, or about 10-fold higher compared to the cellular of the compound of the invention into a second diseased cell.

Diseased and healthy cells contacted by the compound of the invention can be derived from any cell line and/or tissue. For example, in some embodiments, the cell is a from a cancer cell line. Example cancer cell lines include, but are not limited to, SCC-61, rSCC-61, G48, MD3-MD231, MCF-7, HepG2 (hepatocellular carcinoma), HeLa (cervix adenocarcinoma) and ACC1-activated fibroblasts, PC3, NSCLC (non-small cell lung cancer), U118 MG, HCC78, and 3T3 (cholangiocarcinoma). In some embodiments, the cells are from a diseased tissue such as, but not limited to, cancerous tissue, severely damaged neurodegenerative brain tissues, inflammatory tissues including colitis, chronic hepatitis, bacterial infections, cardiovascular/atherosclerotic plaque tissues. In general, the tissue is from a mammal, and in some embodiments the mammal is a human.

In some embodiments, the method of the invention measures the cellular uptake of the compound of the invention in vitro. In some embodiments, the method of the invention measures the amount of hydrogen sulfide ($H_2S$) in vitro. In some embodiments, the method of the invention measures the cellular uptake of the compound of the invention in vivo. In some embodiments, the method of the invention measures the amount of hydrogen sulfide ($H_2S$) in vivo.

In some embodiments, the tissues comprise cancerous tissues for cancer detection or treatment. Cancers may include, e.g., cervical cancer, breast cancer, lung cancer, brain cancer, liver cancer, pancreatic cancer, colon cancer, leukemia, bone cancer, blood cancer, or ovarian cancer. Other imaging applications include, but are not limited to, neuroimaging (e.g., Alzheimer's), diabetes, cardiology (e.g., cardiovascular diseases, atherosclerosis, hypertension, ischemia/reperfusion injury), and rheumatoid arthritis.

In some embodiments, the administering step is carried out by parenteral administration. For example, in some embodiments, the compound of the invention is administered by systemic injection and/or infusion. After administration, imaging the area of interest of the subject is carried out to locate any diseased tissue (e.g., a tumor).

The useful dosage to be administered and the particular mode of administration will vary depending upon such factors as age, weight, and particular region of the subject's body to be imaged, as well as the form of the pharmaceutical formulation. In some embodiments, the compounds of the invention may be included in formulations suitable for oral, rectal, topical, buccal (e.g., sub-lingual), parenteral (e.g., subcutaneous, intramuscular, intradermal, or intravenous) and transdermal administration. For example, formulations of the present invention suitable for parenteral administration conveniently comprise sterile aqueous preparations of the compound of the invention, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood. Examples may also include pharmaceutical formulations comprising a suspension, emulsion, microsphere, liposomes or the like, as will be apparent to those skilled in the art.

In some embodiments, dosage may be administered at lower levels and increased levels until the desirable diagnostic and/or therapeutic effect is achieved. In some embodiments, the compound of the invention may be administered (e.g., by intravenous injection usually in saline solution) at a dose of about 0.1 to about 10-15 mCi per 50-70 kg body weight (and all combinations and subcombinations of dosage ranges and specific dosages therein). Imaging may be performed using techniques well known to the person of ordinary skill in the art.

A composition comprising compounds of the present disclosure may be administered at dosages ranging from about 0.5 µmol/kg to about 1.5 mmol/kg (and all combinations and subcombinations of dosage ranges and specific dosages therein).

Another aspect of the invention relates to a diagnostic kit for the preparation of the radioactive compounds of the invention for imaging hydrogen sulfide ($H_2S$) in a subject. Diagnostic kits of the present invention comprises one or more vials containing a predetermined amount of a compound of the present invention, and optionally one or more pharmaceutically acceptable excipients such as, but not limited to, buffers, stabilizing agents, and/or solvents. In some embodiments, the compound of the present invention is formulated as a pharmaceutically acceptable composition and/or pharmaceutically acceptable formulation, which is part of the diagnostic kit comprising one or more vials containing pharmaceutically acceptable excipients required to produce the active compound of the invention.

III. Formulations of Active Compounds.

The active compounds described herein may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts or prodrugs thereof) is typically admixed with, inter alia, an acceptable carrier. The carrier must, of course, be acceptable in the sense of being compatible with any other ingredients in the formulation and must not be deleterious to the subject. The carrier may be a solid or a liquid, or both, and is preferably formulated with the compound as a unit-dose formulation, for example, a tablet, which may contain from 0.01 or 0.5% to 95% or 99% by weight of the active agent. One or more active agents may be incorporated in the formulations of the invention, which may be prepared by any of the well-known techniques of pharmacy comprising admixing the components, optionally including one or more accessory ingredients.

The pharmaceutical compositions may also contain other additives, such as pH-adjusting additives. In particular, useful pH-adjusting agents include acids, such as hydrochloric acid, bases and/or buffers, such as sodium lactate, sodium acetate, sodium phosphate, sodium citrate, sodium borate, or sodium gluconate. Further, the compositions may contain preservatives. Useful preservatives include methylparaben, propylparaben, benzoic acid and benzyl alcohol.

Formulations of the invention include those suitable for oral, buccal (sub-lingual), parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound being used.

Formulations suitable for oral administration may be presented in discrete units, such as capsules, cachets, lozenges, or tablets, each containing a predetermined amount of the active compound(s); as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations of the present invention suitable for parenteral administration comprise sterile aqueous and non-aqueous injection solutions, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s) in a unit dosage form in a sealed container. The active compound(s) may be provided in the form of a lyophilizate which is capable of being reconstituted with a suitable pharmaceutically acceptable carrier to form a liquid composition suitable for injection thereof into a subject.

When the active compound(s) is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

The amount of active compound(s) administered for therapeutic treatment may depend on the age, weight, and condition of the patient as determined by a physician. The unit dosage form typically comprises from about 1 mg, 5 mg, 10 mg, 100 mg, 250 mg, 500 mg, 1 gram, 5 grams, 10 grams, or any ranges therein, of the active compound(s), depending on the subject being treated (e.g., human or non-human mammalian subject). In some embodiments, the unit dosage form is in the range of 500 mg to 10 grams, keeping in mind that a good portion of the active compound(s) may not be absorbed upon administration (e.g., oral administration).

In some embodiments, the present invention provides a pharmaceutical composition which is utilized in combination with radiation therapy.

The present invention is explained in greater detail in the following non-limiting examples.

EXAMPLES

We set out to develop chemical probes that would not only display remarkable reactivity and selectivity towards $H_2S$, but unprecedented modularity, such that issues related to insufficient water solubility, cell permeability, and/or tissue specificity could be easily addressed. To achieve this desired versatility without comprising reactivity and selectivity, we employed a selenosulfide functionality. Although selenosulfides have been rarely reported within the chemical literature,[19,20] we reasoned that reactivity differences between selenium and sulfur could be exploited such that the selenium half when tethered to a second electrophilic partner would effectively scavenge and detect $H_2S$, while the sulfur half would provide a suitable handle for mediating its physicochemical properties. Therefore, we first synthesized selenosulfide 1 from 3-bromopivalic acid (see Suarez et al., Chem. Eur. J., 25:15736-15740 (2019)) as it provided an amino group for subsequent conjugation reactions. And in an initial effort to afford high biocompatibility, we then appended an acetyl group to access probe AL1 (Scheme 1).

Scheme 1. Synthesis of versatile, reaction-based fluorescent probes for H2S detection.

Our proposed mechanism for H$_2$S detection by AL1 is depicted in Scheme 2. We hypothesized that an initial exchange reaction between H$_2$S and AL1 would quickly generate 2 and N-acetylcysteamine as an innocuous byproduct (note: cysteamine is a prescribed therapeutic for the treatment of corneal cystinosis given its low toxicity and superb antioxidant activity). F. Shams et al, *OPTH* 2014, 2077. With selenium's heightened electrophilic character, nucleophiles will typically attack at selenium much more rapidly than at sulfur. H. J. Reich, R. J. Hondal, *ACS Chem. Biol.* 2016, 11, 821-841. In fact, exchange reactions at selenium have been reported to be orders of magnitude faster than analogous exchange reactions where sulfur serves as the electrophilic partner. D. Steinmann, T Nauser, W. H. Koppenol, *J. Org. Chem.* 2010, 75, 6696-6699; J. C. Lukesh, B. VanVeller, R. T. Raines, *Angew. Chem. Int. Ed.* 2013, 125, 13139-13142. This feature was thought to ensure that our probe would not be consumed by other biothiols—a serious limitation of earlier probes as their attack at selenium would simply regenerate a similar selenosulfide poised for nucleophilic attack by H$_2$S (4, Scheme 2). C. Liu et al, *Angew. Chem. Int. Ed.* 2011, 50, 10327-10329; B. Peng et al, *Org. Lett.* 2015, 17, 1541-1544. We predicted that once intermediate 2 was formed, however, a rapid cyclization event would release the fluorescent reporter and thus confirm the presence of H$_2$S.

Scheme 1. Proposed mechanism for H₂S detection with AL1.

Based on this proposed mechanism, implementation of the gem-dimethyl group was predicted to serve several distinct functions. For one, it was expected to operate as a steric shield, blocking access to the ester carbonyl and shutting down hydrolysis and the direct nucleophilic attack of other biothiols and nucleophiles. In turn, this would reduce background fluorescence and increase the overall selectivity of the probe. Indeed, the introduction of gem-dimethyl groups is a common technique used in medicinal chemistry to improve plasma and chemical stability of biologically active compounds. T. T. Talele, *J. Med. Chem.* 2018, 61, 2166-2210. Secondly, while intermolecular attack at the ester would be diminished, we theorized that the requisite cyclization event was likely to be both thermodynamically and kinetically enhanced by the presence of those same methyl groups as introduction of alkyl substituents is known to favor intramolecular reactions (i.e. The Thorpe-Ingold Effect). M. E. Jung, G. Piizzi, *Chem. Rev.* 2005, 105, 1735-1766.

Example 1: Selectivity for Hydrogen Sulfide (H₂S)

Figure 1:
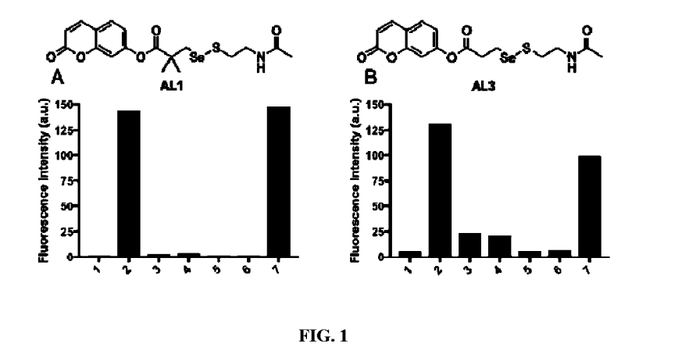
FIG. 1. Fluorescence response ($\lambda_{ex}$: 330 nm) of probes (20 µM) in PBS buffer (pH 7.4), at room temperature, and in the presence of various biological thiols and nucleophiles: (1) PBS buffer alone; (2) 50 µM $Na_2S$; (3) 100 µM cysteine; (4) 1 mM glutathione; (5) 100 µM serine; (6) 100 µM lysine; (7) 1 mM glutathione+50 µM $Na_2S$. (A): Probe AL1 and (B): Probe AL3.

To assess our hypothesis, the selectivity of our design towards H₂S was first assessed by incubating AL1 (20 μM) with various biological thiols and nucleophiles in PBS buffer (FIG. 1A). After reacting for 10 min at room temperature, the resulting turn-on response was gauged using fluorescence spectroscopy. The results from this assay were indeed stunning. In the presence of 50 μM Na₂S (an H₂S equivalent at physiological pH) a greater than 100-fold increase in relative fluorescence intensity was observed. Yet, in the presence of other biologically relevant thiols and nucleophiles, no increase in fluorescence was detected, even when significantly higher concentrations were used. Moreover, this assay confirmed that AL1 is not consumed by the presence of other thiols and that its reactivity towards H₂S is retained in their presence (FIG. 1A, Column 7). To confirm that the gem-dimethyl group affords enhanced differentiation, we also generated AL3 which lacks the steric shield alpha to the ester carbonyl. The same selectivity studies with AL3 unequivocally demonstrate the significance of the gem-dimethyl group as a noticeable reduction in selectivity was observed in their absence (FIG. 1B).

Example 2: Stability of Active Compounds

Figure 2:
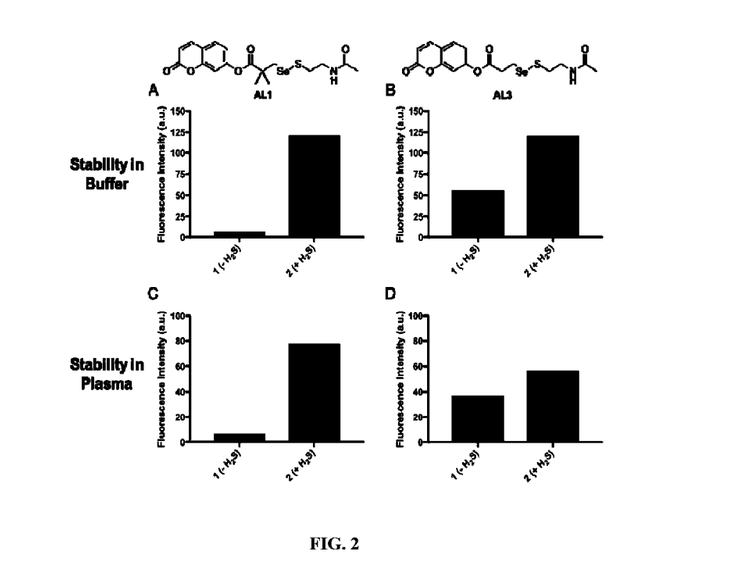
FIG. 2. Fluorescence response ($\lambda_{ex}$: 330 nm) of probes (20 µM) at room temperature and under varying conditions: (A and B): (1): 24 hour incubation period in PBS buffer alone; (2): 24 hour incubation period in PBS buffer followed by the addition of $Na_2S$ (50 µM). (C and D): (1): 10 min incubation period in fetal bovine plasma alone; (2): 10 min incubation period in fetal bovine plasma and in the presence of $Na_2S$ (50 µM). AL1: 2A and 2C and AL3: 2B and 2D.

To further establish the increased durability of AL1 relative to AL3, we tested the stability of both compounds in PBS buffer over a 24 h incubation period (FIGS. 2A and 2B). While AL3 was shown to be highly susceptible to hydrolysis in buffer alone (FIG. 2B, Column 1), AL1 exhibited superb stability during the 24 h period (FIG. 2A, Column 1). Moreover, the subsequent addition of Na₂S to AL1 resulted in impressive turn-on fluorescence (FIG. 2A, Column 2). These results indicate that AL1 is not only resistant to hydrolysis, but that its reactivity towards H₂S is preserved, even after prolonged exposure to buffer. The stability of AL1 and AL3 was also assessed in fetal bovine plasma (FIGS. 2C and 2D). Again, AL1 displayed remarkable stability as little fluorescence was emitted in the absence of Na₂S (FIG. 2C, Column 1). Furthermore, even within this complex environment, AL1 showed a marked turn-on response when Na₂S was present. Probe AL3, on the other hand, underwent significant decomposition in a very short period of time indicating that its ester moiety is significantly more labile, especially in the presence of plasma proteins (FIG. 2D, Column 1).

Example 3: Active Compounds as Quantitative Probes for Hydrogen Sulfide (H₂S)

Figure 3:
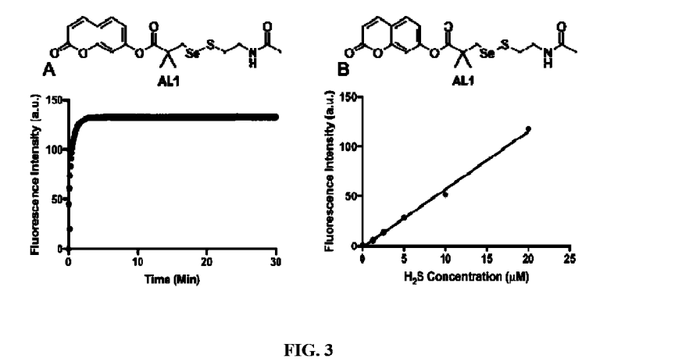
FIG. 3. (A) Time-dependent fluorescence emission ($\lambda_{ex}$: 330 nm) of AL1 (20 µM) in the presence of $Na_2S$ (50 µM). (B) Fluorescence intensity ($\lambda_{ex}$: 330 nm) of AL1 (40 µM) in response to increasing $Na_2S$ concentrations.

The efficiency of AL1 in sensing H₂S in PBS buffer (pH 7.4) and at room temperature was also assessed (FIG. 3A). Under these conditions, the resulting fluorescence intensity reached a maximum in less than two minutes, highlighting that our designed probe is not only selective but also highly reactive towards H₂S—a necessary feature for detecting analytes which are short-lived. To determine if AL1 could also be used to detect H$_2$S quantitatively in buffer, the resulting fluorescence was measured in response to a series of different concentrations of H$_2$S (FIG. 3B). Indeed, the ensuing fluorescence intensity increased in a linear fashion in the range of 0-20 µM H$_2$S and with a detection limit of 0.05 µM.

Figure 4:
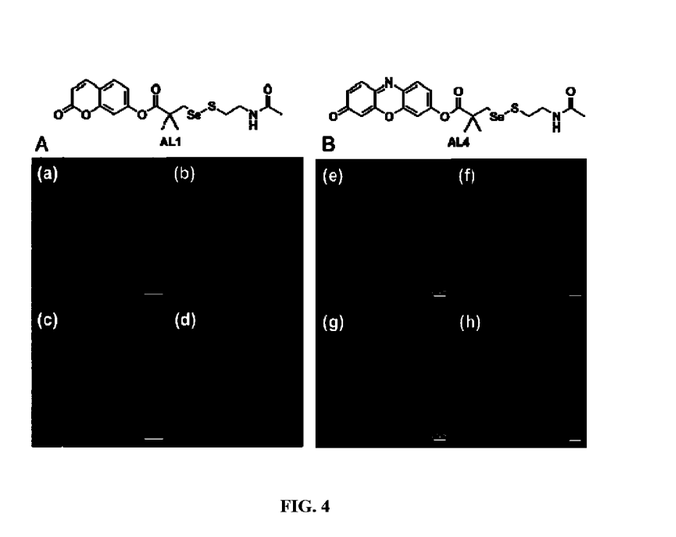
FIG. 4. (A) Visualization of $H_2S$ in live HeLa cells with AL1 (12.5 µm). Imaging: ex: 405 nm, em: 452 nm. (a and b): No $Na_2S$ added (control); (c and d): Addition of $Na_2S$ (50 µm). Scale bar is set to 20 µm. (B) Visualization of $H_2S$ in live HeLa cells with AL4 (5 µm). Imaging: ex: 561 nm, em: 587 nm. (e and f): No $Na_2S$ added (control); g and h: Addition of $Na_2S$ (25 µM). Scale bar is set to 20 µm.

Example 4: Active Compounds for Use in Imaging Hydrogen Sulfide (H$_2$S) in Live Cells Probe AL1 was also shown to be useful in imaging H$_2$S in live cells using confocal microscopy. Cultured HeLa cells were incubated with AL1 (12.5 µM) for 45 min and then washed to remove any excess probe. Under these conditions we did not observe any fluorescent cells, signifying that AL1 was indeed stable within a cellular environment (FIG. 4A). However, upon treatment with 50 µM Na$_2$S, a strong blue fluorescence within cells was observed. To show that our framework was highly adaptable, we also generated AL4 and assessed its ability to visualize H$_2$S in live cells. Probe AL4 utilizes resorufin as its latent fluorescent reporter which has the added benefit of longer excitation and emission wavelengths, further boosting its potential in tissue imaging applications. Under similar conditions, a strong fluorescence was again observed within HeLa cells upon treatment with AL4 (5 µM) and Na$_2$S (25 µM) (FIG. 4B).

Figure 5:
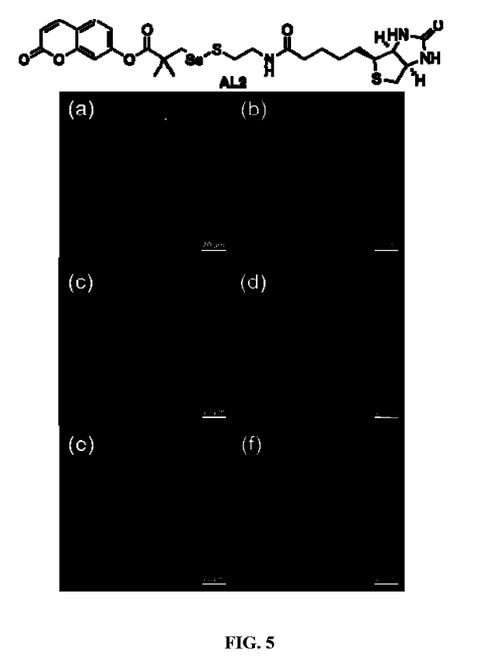
FIG. 5. Fluorescence images of live HeLa cells treated with AL2 (10 µM); (a and b): No $Na_2S$ (control); (c and d): Addition of $Na_2S$ (50 µM); (e and f): Fluorescence images of HeLa cells pretreated with biotin (2 mM) followed by treatments with AL2 (10 µM) and $Na_2S$ (50 µM). Imaging: ex: 405 nm, em: 452 nm. Scale bar is set to 20 µm.
Figure 6:
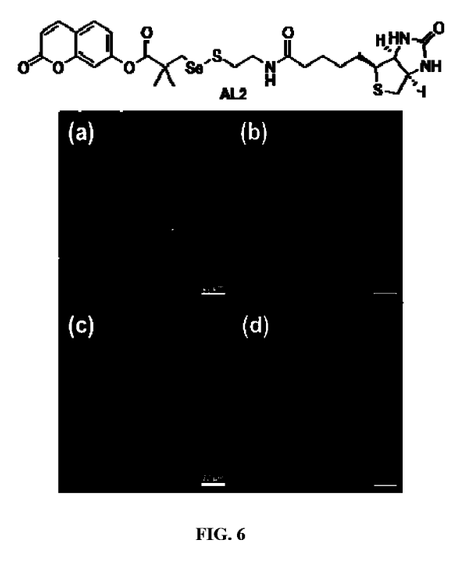
FIG. 6. Fluorescence images of live HEK293 cells. (a and b): Treatment with AL2 (10 µM) alone; (c and d): Treatment with AL2 (10 µM) followed by treatment with $Na_2S$ (50 µM). Imaging: ex: 405 nm, em: 452 nm. Scale bar is set to 20 µm.

Example 5: Active Compounds as Cancer Cell-Specific Hydrogen Sulfide (H$_2$S) Probes We next set to out to showcase the high versatility of our design by demonstrating that we could target selenosulfide 1 to specific tissue or cell types by simply modifying its sulfide linker. As a proof of concept we generated AL2, a cancer cell-specific H$_2$S probe, by coupling biotin to its amine handle (Scheme 1). W. X. Ren et al, *Chem. Commun.* 2015, 51, 10403-10418; X. Song et al, *RSC Adv.* 2017, 7, 15817-15822; M. H. Lee et al, *Chem. Soc. Rev.* 2018, 47, 28-52. Fluorescence imaging experiments were then conducted using both a biotin positive (HeLa) and biotin negative (HEK293) cell line to confirm its selective targeting and delivery. As seen in FIG. 5, when HeLa cells were treated with AL2 alone, minimal fluorescence was witnessed within cells. However, upon the addition of Na$_2$S, a strong blue fluorescent signal was emitted from within, confirming both the intracellular delivery of 7 and its high selectivity towards H$_2$S. To confirm that AL2 was targeting biotin cell surface receptors, in a separate experiment, HeLa cells were pre-treated with biotin prior to the addition of AL2. Under these conditions, the subsequent addition of Na$_2$S did not produce any fluorescence within cells, denoting that the intracellular delivery of AL2 was in fact mediated via biotin transporters (FIGS. 5e and 5f). The selectivity of AL2 was further established using HEK293 (noncancerous human embryonic kidney) cells. Under identical conditions, negligible fluorescence was observed, even upon the addition of exogenous Na$_2$S, indicating that the cellular uptake of AL2 within HEK293 cells (biotin negative) was much less efficient (FIG. 6).

Example 6: Active Compounds as Diagnostic Tools for Identifying Cancers

With many forms of cancer having increased expression of H$_2$S-producing enzymes, cancer-cell specific probes such as AL2 may prove useful in elucidating the roles of H$_2$S in cancer initiation and progression. C. Szabo et al, *Proc. Natl. Acad. Sci. USA* 2013, 110, 12474-12479; D. Wu et al, *Nitric Oxide* 2015, 50, 38-45; Q. Cao et al, *Antiox. Redox Signal.* 2010, 12, 1101-1109; W. Cai et al, *Cell Biol. Intl* 2010, 34, 565-572; K. Módis et al, *Nitric Oxide* 2014, 41, 146-156; C. Chao et al, *Mol. Med.* 2016, 22, 361-379.

Additionally, we note that this technology may also find utility as a diagnostic for certain cancers where both a specific cell surface receptor (e.g. biotin, folate, B12, etc.) and H$_2$S are highly over-expressed as the demonstrated tissue specificity of our H$_2$S-selective probe provides a convenient dual-biomarker for turn-on fluorescence. M. F. Hansen et al, *Cell. Signal.* 2015, 27, 1356-1368; C. Zhang et al, *Chem. Sci.* 2019, 10, 1945-1952.

Finally, given our proposed mechanism for H$_2$S detection (Scheme 2), and the fact that 3 is cleanly generated as a byproduct (see Suarez et al., *Chem. Eur. J.,* 25:15736-15740 (2019)), scaffolds similar to AL2 may be advantageous for the specific capture and removal of H$_2$S within cancerous cells and tissue. Moreover, with high expression levels of H$_2$S being linked to several diseases, its precise downregulation may prove beneficial (C. Yang et al, *Angew. Chem. Int. Ed.* 2019, 58, 10898-10902), highlighting the potential for selenosulfies, and frameworks akin to AL1 and AL2, for serving as useful theranostics.

In closing, we have successfully shown that selenosulfides tethered to gem-dimethyl esters are exceptional frameworks for H$_2$S probe development. In addition to their high reactivity and selectivity towards H$_2$S, their remarkable versatility allows for their physicochemical properties to be easily tuned through structural modifications of their sulfide handle. Given the distinct chemical differences of both sulfur and selenium, we foresee the use of selenosulfides as a global strategy for tuning the physicochemical and biological properties of molecular cargo.

The foregoing is illustrative of the present invention, and is not to be construed as limiting thereof. The invention is defined by the following claims, with equivalents of the claims to be included therein.

What is claimed is:

1. A compound of formula I:

I wherein:

R¹ is a fluorescent reporter moiety, wherein said fluorescent reporter moiety has little or negligible fluorescence in the compound of formula I, but provides increased fluorescence upon cleavage from the compound of formula I upon reaction with hydrogen sulfide (H₂S);

R² is a physicochemical modulator selected from the group consisting of:

wherein the wavy line indicates covalent attachment point to the sulfur atom of the compound; and W is O, S, or NH, or a pharmaceutically acceptable salt of the compound of formula I.

2. The compound of claim 1, wherein the fluorescent reporter moiety is selected from the group consisting of:

, and wherein the wavy line indicates covalent attachment point to the W of the compound.

3. The compound of claim 1, wherein said compound is:

AL1

AL2 or a pharmaceutically acceptable salt or prodrug thereof.

4. A composition comprising a compound of claim 1 and a pharmaceutically acceptable carrier.

5. The composition of claim 4, wherein said composition is formulated for oral or parenteral administration.

6. The composition of claim 4, wherein said composition is formulated for intravenous administration.

7. The compound of claim 1, wherein W is O.

8. The compound of claim 1, wherein R2² is:

9. A compound having the structure:

or a pharmaceutically acceptable salt thereof.

10. A compound having the structure:

or a pharmaceutically acceptable salt thereof.

11. The compound of claim 1, wherein said compound is:

or a pharmaceutically acceptable salt thereof.

12. The compound of claim 1, wherein said compound is:

or a pharmaceutically acceptable salt thereof.

13. The compound of claim 1, wherein said compound is:

or a pharmaceutically acceptable salt thereof.

* * * * *

UNITED STATES PATENT AND TRADEMARK OFFICE
CERTIFICATE OF CORRECTION

PATENT NO. : 11,931,428 B2
APPLICATION NO. : 16/947869
DATED : March 19, 2024
INVENTOR(S) : John C. Lukesh, III It is certified that error appears in the above-identified patent and that said Letters Patent is hereby corrected as shown below:

In the Specification

Column 5, Line 19: Please correct "0" to read --O--

Column 8, Line 3: Please correct "0" to read --O--

Column 15, Scheme 1: Please correct "High Blocompatibility" to read --High Biocompatibility--

Column 18, Scheme 1, Compound 2: Please delete compound 2 and replace with the following:

In the Claims

Column 25, Line 17, Claim 8: Please correct "R2$^2$" to read --R$^2$--

Column 26, Lines 50-55, Claim 13: Please delete compound AL4 and replace with the following:

Signed and Sealed this
Fourth Day of February, 2025

Coke Morgan Stewart
*Acting Director of the United States Patent and Trademark Office*